(12) United States Patent
Sambusseti et al.

(10) Patent No.: US 10,441,405 B2
(45) Date of Patent: Oct. 15, 2019

(54) ORTHOTOPIC ARTIFICIAL BLADDER ENDOPROSTHESIS

(71) Applicants: Antonio Sambusseti, Cremona (IT); Gianni Cancarini, Brescia (IT)

(72) Inventors: Antonio Sambusseti, Cremona (IT); Gianni Cancarini, Brescia (IT)

(*) Notice: Subject to any disclaimer, the term of this patent is extended or adjusted under 35 U.S.C. 154(b) by 0 days.

(21) Appl. No.: 15/515,043

(22) PCT Filed: Sep. 28, 2015

(86) PCT No.: PCT/IB2015/057424
§ 371 (c)(1),
(2) Date: Mar. 28, 2017

(87) PCT Pub. No.: WO2016/051330
PCT Pub. Date: Apr. 7, 2016

(65) Prior Publication Data
US 2017/0216012 A1     Aug. 3, 2017

(30) Foreign Application Priority Data

Sep. 30, 2014  (IT) .............................. MI2014A1706

(51) Int. Cl.
*A61F 2/04* (2013.01)
*A61L 27/18* (2006.01)
*A61L 27/30* (2006.01)

(52) U.S. Cl.
CPC ...... *A61F 2/042* (2013.01); *A61F 2210/0004* (2013.01); *A61F 2230/0071* (2013.01); *A61F 2250/0003* (2013.01); *A61F 2250/0059* (2013.01); *A61L 27/18* (2013.01); *A61L 27/303* (2013.01); *A61L 2430/22* (2013.01)

(58) Field of Classification Search
CPC ........................................................ A61F 2/042
See application file for complete search history.

(56) References Cited

U.S. PATENT DOCUMENTS 4,219,026 A    8/1980 Layton
4,655,745 A    4/1987 Corbett
(Continued)

FOREIGN PATENT DOCUMENTS

DE    102010024820 A1    12/2011
FR    2116838 A5 *    7/1972    ............. A61F 2/042
(Continued)

OTHER PUBLICATIONS

Lukacz et al. "A healthy bladder: a consensus statement." Int J Clin Pract. Oct. 2011; 65(10): 1026-1036.*
(Continued)

*Primary Examiner* — William H Matthew
(74) *Attorney, Agent, or Firm* — Vorys, Sater, Seymour and Pease LLP

(57) ABSTRACT

An orthotopic artificial bladder endoprosthesis includes a casing made of a PGA fiber fabric; the casing having two first connectors for the connection with the ureters of a patient and a further connector for the connection with the urethra of a patient; an inflatable element inserted in the casing; the inflatable element being switchable between an inflated configuration, in which it supports and maintains in position the casing, and a deflated configuration.

19 Claims, 2 Drawing Sheets

(56) References Cited

U.S. PATENT DOCUMENTS

| | | | |
|---|---|---|---|
| 5,518,498 A | 5/1996 | Lindenberg et al. | |
| 6,048,330 A | 4/2000 | Atala | |
| 6,296,668 B1 | 10/2001 | Desgrandchamps et al. | |
| 6,682,473 B1 * | 1/2004 | Matsuura | A61B 5/205 600/29 |
| 6,855,126 B2 | 2/2005 | Flinchbaugh | |
| 7,074,178 B2 * | 7/2006 | Connors | A61B 5/205 600/29 |
| 8,647,358 B2 * | 2/2014 | Brister | A61F 5/0043 606/191 |
| 2004/0243104 A1 | 12/2004 | Seddon | |
| 2005/0065468 A1 | 3/2005 | Goebel | |
| 2005/0124978 A1 | 6/2005 | Kim | |
| 2006/0229553 A1 | 10/2006 | Hammack et al. | |
| 2007/0219488 A1 | 9/2007 | Francescatti | |
| 2007/0276507 A1 | 11/2007 | Bertram et al. | |
| 2008/0097467 A1 | 4/2008 | Gruber et al. | |
| 2009/0118829 A1 * | 5/2009 | Powell | A61F 2/12 623/8 |
| 2010/0010478 A1 | 1/2010 | Nissenkorn | |
| 2010/0324540 A1 | 12/2010 | Paulen et al. | |
| 2011/0196197 A1 * | 8/2011 | Forsell | A61B 17/0469 600/37 |
| 2011/0276081 A1 | 11/2011 | Kilemnik | |
| 2012/0232652 A1 * | 9/2012 | Mora | A61F 2/12 623/8 |
| 2013/0158522 A1 | 6/2013 | Lisowsky et al. | |
| 2014/0214175 A1 | 7/2014 | Barron et al. | |
| 2015/0223924 A1 | 8/2015 | Sambusseti et al. | |
| 2015/0223953 A1 | 8/2015 | Pendleton et al. | |
| 2017/0231748 A1 | 8/2017 | Sambusseti | |

FOREIGN PATENT DOCUMENTS

| | | | |
|---|---|---|---|
| FR | 2759575 A1 | 8/1998 | |
| WO | 9850100 A1 | 11/1998 | |
| WO | 0178576 A2 | 10/2001 | |
| WO | 2007075545 A2 | 7/2007 | |
| WO | 2007095193 A2 | 8/2007 | |
| WO | 2008048764 A1 | 4/2008 | |
| WO | WO 2011160875 A1 * | 12/2011 | A61F 2/042 |
| WO | 2012120326 A1 | 9/2012 | |
| WO | 2014057444 A1 | 4/2014 | |
| WO | 2014060911 A1 | 4/2014 | |
| WO | 2015159185 A1 | 10/2015 | |
| WO | 2016051333 A1 | 4/2016 | |

OTHER PUBLICATIONS

International Search Report and Written Opinion dated Jan. 14, 2016 for PCT/IB2015/057424 to Antonio Sambusseti et al. filed Sep. 28, 2015.

Machine Translation for FR2116838 A5, published Jul. 21, 1972, Applicant: Sowinski Kazimierz Maria.

University of Colorado Hospital. "The Orthotopic Neobladder". pp. 1-8. Oct. 2006.

* cited by examiner

ORTHOTOPIC ARTIFICIAL BLADDER ENDOPROSTHESIS

CROSS-REFERENCE TO RELATED APPLICATIONS

This is a § 371 National Stage Application of International Application No. PCT/IB2015/057424 filed on Sep. 28, 2015, claiming the priority of Italian Patent Application No. MI2014A001706 filed on Sep. 30, 2014.

FIELD OF THE INVENTION

The present invention refers to an orthotopic artificial bladder endoprosthesis.

The application of the present invention lies in the replacement of a bladder of a patient, if the latter is suffering from incurable diseases serious as to compromise the correct function thereof.

BACKGROUND OF THE INVENTION

Known bladder endoprostheses comprise a balloon casing made with an impermeable layered silicone membrane covered with a layer made of biocompatible and biodegradable material. According what is known, the biocompatible and biodegradable covering material is a fabric made of PGA fiber.

The casing is sufficiently rigid so as to stably keep its shape and flexible such that it can be manually compressed to ensure that it empties.

The casing has a connection element located at a lower portion of the casing to connect with the patient's urethra. Similarly, two connection bodies are located at the top to enable connection with the ureters.

The connection bodies are also covered with the biodegradable material.

Following the implant of the endoprosthesis in the patient, there is the formation of a musculo-fibrous tissue layer or fibrous capsule (not impermeable) around the covering of the casing, while the biodegradable material decomposes. In such a manner, a neobladder is generated around the endoprosthesis.

During the resorption, there is the formation of a transition epithelium layer, which is also called urothelium, which is advantageously impermeable. This is essential for ensuring the correct functioning of the prosthesis and of the neobladder that is being formed.

The obtainment of this type of endoprosthesis is complex and costly.

Indeed, the covering made of biocompatible and biodegradable material must be obtained in order to fit on the silicon casing.

In fact, extreme precision is necessary for the correct relative sizing of casing and covering. It is known that the covering also covers the connectors.

This renders the obtainment complex, long and costly.

Other known solution as, for example, in WO2014/057444 discloses an orthotopic artificial bladder endoprosthesis comprising a cuff substantially rigid and shaped as a balloon and comprising an inner surface and an outer surface defining a space suitable for the containment of the urine; according to said solution the rigidity of the cuff and their stable and extended position is obtained by using layers of material made of multilayered silicone suitable for obtaining a cuff sufficiently rigid so as to maintain a balloon shape and, at same time, sufficiently flexible so as to allow deformation caused by external pressure aimed to drain the bladder itself.

Another solution is disclosed in WO98/50100 as a device suitable for feeding an under pressure fluid inside a balloon inserted in a body chamber and aimed to allow and cause a tissue expansion of said cavity affected by a pathology.

Other known documents, such as WO2007/075545, disclose a catheter or a device to drain liquid from a body cavity or from a cavity obtained by surgery, with said device comprising a shaft, an expandable balloon connected to an end of the shaft, a permeable layer arranged outside the expandable balloon and with the shaft comprising a duct discharging the drainage liquid and also comprising a duct for feeding under pressure fluid in the balloon so as to inflate said balloon.

Another document, U.S. Pat. No. 4,219,026, discloses a bladder hemostatic catheter having an elongated shaft provided with a duct or lumen extending along the shaft and also comprising an inflatable balloon made of elastic material covering the distal end of the shaft and with said balloon that when inflated takes a substantially spherical shape suitable to fill the bladder and to exert the pressure requested for terminating the hemorrhages.

An artificial bladder prosthesis in disclosed also in FR2759575 as comprising a containment element made of a double layered material comprising an inner layer and an outer layer made of different materials and with said different material suitable for allowing the implant of the containment element in the patient body avoiding transplant rejection and avoiding drawbacks related to the fact that the urine in the containment element can damage the containment element itself and, furthermore, said double layered material id realized with the aim to keep the rigid shape of the containment element itself.

Another artificial bladder is disclosed in WO2007/095193, as defined by a structure comprising two hemispherical portions joined one to the other and provided with outer flanges suitable for allowing a manipulation of said portions prior or during the surgery and also for allowing the connection of said two portions.

All the known solutions for bladder prosthesis are complex under a constructional point of view, the implant or surgery and so on and, as a consequence, they are costly.

SUMMARY OF THE INVENTION

In this context, the technical task underlying the present invention is to propose an orthotopic artificial bladder endoprosthesis which overcomes the abovementioned drawbacks of the prior art.

In particular, object of the present invention is to provide an orthotopic artificial bladder endoprosthesis that is simpler and quicker to make.

The specified technical task and the specified object are substantially achieved by an orthotopic artificial bladder endoprosthesis comprising the technical characteristics set forth in one or more of the enclosed claims.

BRIEF DESCRIPTION OF THE DRAWINGS

Further characteristics and advantages of the present invention will be clearer from the exemplifying and therefore non-limiting description of a preferred but not exclusive embodiment an orthotopic artificial bladder endoprosthesis, as illustrated in the enclosed drawings, in which.

DETAILED DESCRIPTION OF THE PREFERRED EMBODIMENTS

Figure 1:
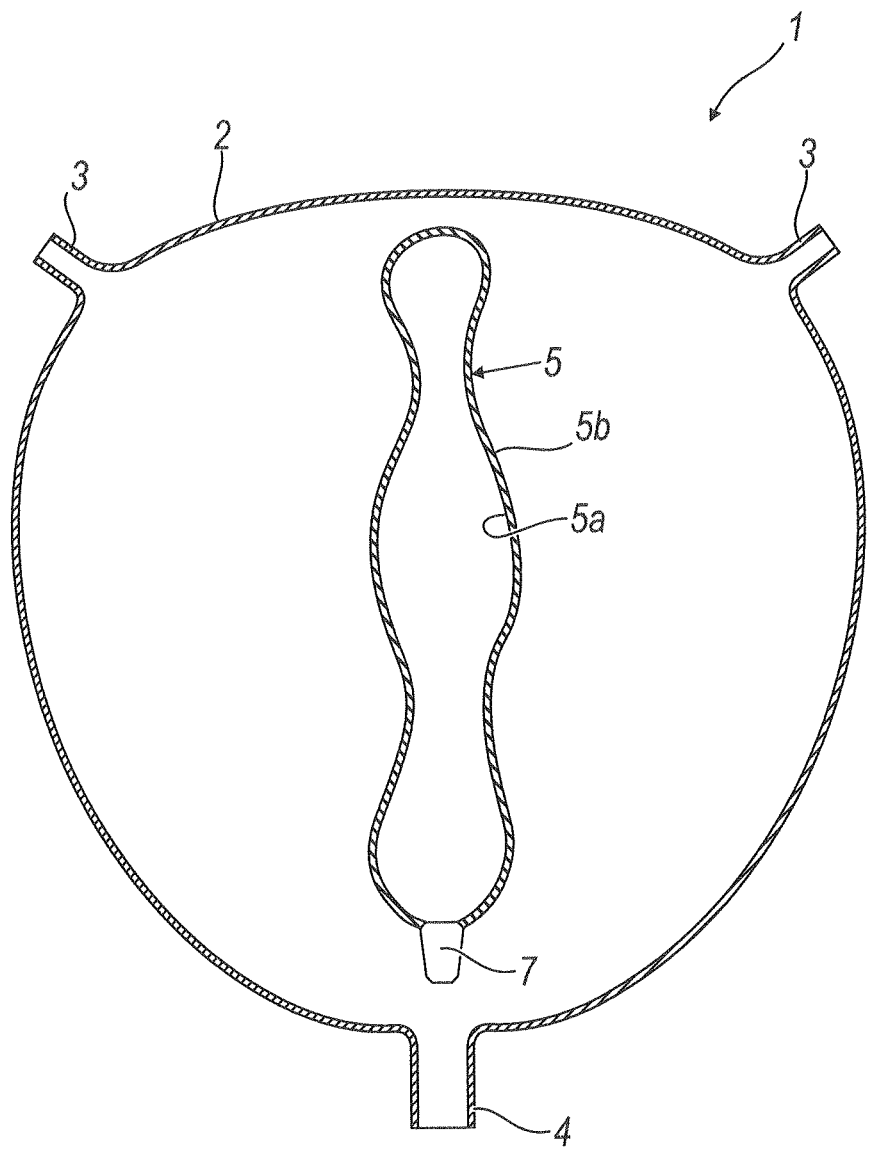
FIG. 1 is a schematic view of an orthotopic artificial bladder endoprosthesis in accordance with the present invention in a first configuration.

With reference to the enclosed drawings, reference number 1 overall indicates an orthotopic artificial bladder endoprosthesis in accordance with the present invention.

The endoprosthesis 1 comprises a casing 2 made with a PGA fiber fabric.

The PGA (polyglycolide or polyglycolic acid) used in the fabric—with which the casing 2 is obtained—is preferably homopolymer. PGA is a highly biocompatible and resorbable polymer that is resistant to urine. In detail, the resorption time of PGA is approximately one month.

The fabric of the casing 2 can be obtained by weaving the PGA thread in various ways, giving rise to a knitted fabric, a woven fabric or a non-woven fabric.

Preferably, the fabric of the casing 2 is a knitted fabric, still more preferably a warp knitted fabric.

In such cases, the fabric of the casing 2 has a rougher surface capable of assuming a net configuration with sufficiently small meshes.

In detail, its weft is such that its interstitial space is less than 200 $\mu m$, preferably around 160 $\mu m$, corresponding to an average area of the holes equal to approximately 0.02 $mm^2$. This ensures impermeability to urine, preventing leaks.

Furthermore, once the endoprosthesis 1 is inserted, the covering is impregnated with blood and in particular with plasma, which allows the antibiotic drugs to be effective.

Furthermore, the fabric of the casing 2 is preferably textured so as to give it even greater surface roughness and greater rigidity and impermeability. The greater roughness of the fabric limits the risk of adhesion of the fibrous capsule.

Purely by way of example, the fabric of the casing 2 has a thickness substantially comprised between 0.3 mm and 0.6 mm, more preferably comprised between 0.4 mm and 0.53 mm, still more preferably being substantially 0.45 mm.

In addition, the thread with which the fabric of the casing is obtained has a density comprised between 50 and 200 denier.

The casing 2 substantially has a spherical shape and has first connectors 3 intended to be connected, by means of resorbable suture, with the ureters of a patient.

The casing 2 also has a second connector 4 intended to be connected, by means of resorbable suture, to the urethra of a patient.

The casing 2 can be obtained by means of joining two hemispherical caps. Alternatively, the casing 2 can be obtained in a single piece.

Purely by way of example, the casing 2 has a volume comprised between 300 $cm^3$ and 400 $cm^3$, preferably substantially equal to 350 $cm^3$.

The endoprosthesis 1 also comprises an inflatable element 5 placed within the casing 2.

Figure 2:
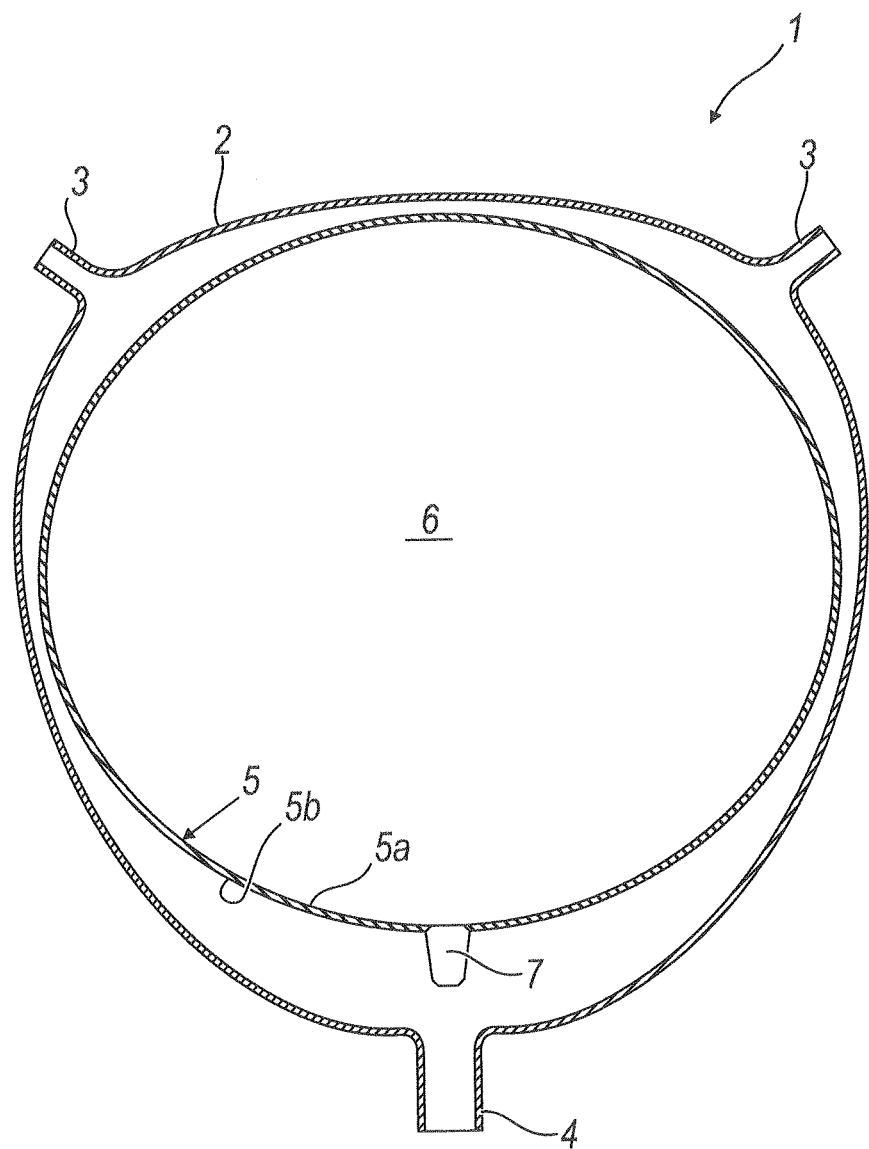
FIG. 2 is a schematic view of the endoprosthesis of FIG. 1 in a second configuration.

The inflatable element 5 is switchable between an inflated configuration (FIG. 2) and a deflated configuration (FIG. 1).

In the inflated configuration, the inflatable element 5 supports the casing 2 in an enlarged, taut and operative configuration.

The inflated configuration is maintained for the entire time necessary for the formation of the neobladder, which occurs at the same time as the progressive dissolution of the PGA casing 2.

Normally, as stated, the time necessary for the dissolution of the PGA fibers is approximately one month.

Therefore, the inflatable element 5 in the inflated configuration has a structural function for the casing 2.

Purely by way of example, the inflatable element 5 has, in the inflated configuration, a volume comprised between 300 $cm^3$ and 400 $cm^3$, preferably substantially equal to 350 $cm^3$.

The deflated configuration is instead selected during the step of storing the endoprosthesis 1 before its implant in the patient. Furthermore, the deflated configuration is restored when, following the dissolution of the casing 2, the neobladder is formed and the inflatable element 5 must be removed, by way of example, by means of cystostomy.

The inflatable element 5 is constituted by a silicone membrane. Preferably, the inflatable element 5 is constituted by a multilayer silicone membrane.

Purely by way of example, the membrane comprises substantially 20 layers, each of approximately 30 $\mu m$ thickness.

The membrane with which the inflatable element 5 is obtained has a thickness comprised between 500 $\mu m$ and 700 $\mu m$, preferably the thickness of the membrane is substantially 600 $\mu m$.

The inflatable element 5 has an internal surface 5a directed towards an enclosure 6 for containing a fill fluid.

In addition, the inflatable element 5 has an external surface 5b internally directed towards the casing 2. Advantageously, the external surface 5b of the inflatable element 5 is covered with a layer of turbostratic pyrolytic carbon.

The turbostratic pyrolytic carbon layer has a thickness comprised between 0.2 $\mu m$ and 0.3 $\mu m$.

The application of the carbon layer on the external surface 5b of the inflatable element 5 allows avoiding the risk that the fibrous capsule being formed could adhere to the casing 2 itself. In addition, the layer of turbostratic pyrolytic carbon prevents the formation of crusts due to urine.

The application of the carbon layer on the external surface 5b also allows protecting the inflatable element 5 from the corrosion caused by urine.

In the inflated configuration, the inflatable element 5 has a substantially spherical shape.

The inflatable element 5 also has a valve 7, which allows introducing and extracting a fill fluid in the enclosure 6 interior.

Purely by way of example, the fill fluid is a physiological solution.

It is observed that the inflatable element 5 is independent of the casing 2. In other words, the inflatable element 5 is completely detached from the casing 2. In still other words, no connection means of any type are provided arranged between the casing 2 and the inflatable element 5.

More particularly, the valve 7 is independent of the first connectors 3 and/or of the second connector 4. In other words, the valve 7 is not in any way connected with the first connectors 3 and/or the second connector 4.

It is also observed that the inflatable element 5 is inserted in the casing 2 during the manufacturing of the endoprosthesis 1.

During use, the endoprosthesis 1 in accordance with the present invention is implanted once the natural bladder of the patient, e.g. compromised by a serious disease, is removed.

Once the connections with the ureters have been obtained, as stated by means of resorbable sutures, the inflatable element 5 is brought into the inflated configuration. In order to do this, the surgeon identifies the valve 7, e.g. by means of suitable diagnostic instruments, and reaches it, through the second connector 4, with a duct for transferring physiological solution through the patient's urethra. The surgeon then accesses the enclosure 6 and fills it with the physiological solution until the enclosure 6 and filled in the correct manner.

Once the valve 7 is disengaged and the correct inflation of the inflatable element 5 is verified together with its positioning, the second connector 4 is fixed to the urethra by means of resorbable suture and the operation site is reclosed.

At this point, it is necessary to wait the pre-established time period in order to allow the reconstruction of the neobladder.

After said period has passed, the surgeon reopens the operation site and brings the inflatable element 5 back into the deflated configuration. Its function has now terminated, since the neobladder has been successfully formed.

Once the inflatable element 5 is deflated, the surgeon cuts the neobladder so as to access its interior, tracing the now-deflated inflatable element 5 in order to extract it.

The subsequent reclosure of the neobladder and of the operation site concludes the implant operation of the endoprosthesis 1.

In addition, a urine drain tube (not illustrated) can be provided, which is inserted in the urethra of the patient.

The drain tube goes beyond the sphincter of the patient and reaches the second connector 4, and is fixed thereto. The end of the drain tune comprises a Dacron® mesh in order to achieve the connection.

The drain tube is made of silicone and is (internally and/or externally) covered with a layer of turbostratic pyrolytic carbon in order to prevent crusts.

The drain tube has minimum length of 15 cm.

The drain tube has a substantially circular section. The internal diameter is approximately 6 mm while the external diameter is approximately 9 mm.

The invention thus described attains the preset object.

Indeed, the use of the inflatable element, and its introduction in the PGA casing during manufacture of the endoprosthesis, allows a considerable simplification of the attainment of the endoprosthesis itself.

Indeed, the casing made of resorbable fabric and the inflatable element are obtained independent of each other and particular expedients and precision are not required.

The invention claimed is:

1. An orthotopic artificial bladder endoprosthesis for insertion into a patient configured to enable formation of a neobladder comprising:
a casing made of a PGA fiber fabric configured to resorb over approximately one month; the casing having two first connectors for connection with the ureters of the patient and a second connector for connection with the urethra of the patient; and
an inflatable element inserted in the casing and being independent of the casing; the inflatable element being switchable between an inflated configuration, in which the inflatable element is configured to support and maintain in position the casing the entire time necessary for the formation of a neobladder occurring at the same time as the progressive dissolution of the PGA casing in one month, and a deflated configuration,
wherein the inflatable element comprises a membrane having an external surface, wherein the membrane of the inflatable element has an internal surface directed towards and defining an enclosure,
wherein the inflatable element has a valve for introducing and extracting a fill fluid for expanding the inflatable element to the inflated configuration in which the inflatable element supports and maintains in position the casing,
wherein the valve directly protrudes from the inflatable element,
wherein the inflatable element defines the enclosure for the fill fluid, the valve being in direct communication with the enclosure,
the valve adapted and configured to be within the casing when the inflatable element is in the inflated configuration,
wherein in the inflated configuration the inflatable element extends across the casing to support opposed sides of the casing, wherein in the inflated configuration the inflatable element has a volume between 300 $cm^3$ and 400 $cm^3$ and the casing has a volume between 300 $cm^3$ and 400 $cm^3$.

2. The endoprosthesis according to claim 1, wherein the inflatable element has an external surface covered with turbostratic pyrolytic carbon.

3. The endoprosthesis according to claim 1, wherein the inflatable element has a spherical shape in the inflated configuration.

4. The endoprosthesis according to claim 1, wherein the inflatable element is constituted by a silicone membrane and the valve for introducing and extracting the fill fluid is directly protruding from the silicone membrane;
wherein the inflatable element membrane and valve are within the casing.

5. The endoprosthesis according to claim 4, wherein the valve is independent of the first connectors and/or the second connector.

6. The endoprosthesis according to claim 1, wherein the inflatable element membrane is constituted by a multilayer silicone membrane.

7. The endoprosthesis according to claim 1, wherein in the inflated configuration the inflatable element volume is between 300 $cm^3$ and 350 $cm^3$ and the casing volume is between 300 $cm^3$ and 400 $cm^3$.

8. The endoprosthesis according to claim 3, wherein the valve is independent of the first connectors and the second connector.

9. The endoprosthesis according to claim 1, wherein the valve is independent of the first connectors and/or the second connector.

10. The endoprosthesis according to claim 2, wherein the inflatable element membrane is constituted by a multilayer silicone membrane.

11. The endoprosthesis according to claim 3, wherein the inflatable element membrane is constituted by a multilayer silicone membrane.

12. The endoprosthesis according to claim 1, wherein the PGA fabric of the casing has a thickness between 0.3 mm and 0.6 mm.

13. The endoprosthesis according to claim 1, wherein the PGA fabric of the casing has a thickness between 0.4 mm and 0.53 mm.

14. The endoprosthesis according to claim 4, wherein the inflatable element is completely detached from the casing.

15. The endoprosthesis according to claim 1, wherein the inflatable element valve for introducing and extracting the fill fluid is within the casing.

16. The endoprosthesis according to claim 15, wherein the inflatable element valve has opposed first and second ends, the first end attached to the inflatable element, the second end freely extending to be exposed to an interior cavity of the casing.

17. An orthotopic artificial bladder endoprosthesis for insertion into a patient configured to enable formation of a neobladder comprising:
- a casing made of a PGA fiber fabric configured to resorb over approximately one month; the casing having two first connectors for connection with the ureters of the patient and a second connector for connection with the urethra of the patient; and
- an inflatable element inserted in the casing and being independent of the casing; the inflatable element being switchable between an inflated configuration, in which the inflatable element is configured to support and maintain in position the casing the entire time necessary for the formation of a neobladder occurring at the same time as the progressive dissolution of the PGA casing in one month, and a deflated configuration,
- wherein the inflatable element comprises a membrane having an external surface, wherein the membrane of the inflatable element has an internal surface directed towards and defining an enclosure,
- wherein the inflatable element has a valve for introducing and extracting a fill fluid for expanding the inflatable element to the inflated configuration in which the inflatable element supports and maintains in position the casing,
- wherein the valve directly protrudes from the inflatable element,
- wherein the inflatable element defines the enclosure for the fill fluid, the valve being in direct communication with the enclosure,
- the valve adapted and configured to be within the casing when the inflatable element is in the inflated configuration,
- wherein in the inflated configuration the inflatable element extends across the casing to support opposed sides of the casing,
- wherein the inflatable element valve for introducing and extracting the fill fluid is within the casing, wherein the inflatable element valve has opposed first and second ends, the first end attached to the inflatable element, the second end freely extending to be exposed to an interior cavity of the casing.

18. The endoprosthesis according to claim 17, wherein the inflatable element has an external surface covered with turbostratic pyrolytic carbon.

19. The endoprosthesis according to claim 17, wherein the inflatable element membrane is constituted by a multilayer silicone membrane.

* * * * *